United States Patent
Smith

(10) Patent No.: US 11,053,206 B2
(45) Date of Patent: Jul. 6, 2021

(54) HYDROFLUOROCARBOXIMIDATE AND METHODS OF MAKING AND USING THE SAME

(71) Applicant: 3M INNOVATIVE PROPERTIES COMPANY, St. Paul, MN (US)

(72) Inventor: Sean M. Smith, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 26 days.

(21) Appl. No.: 16/634,707

(22) PCT Filed: Aug. 23, 2018

(86) PCT No.: PCT/US2018/047621
§ 371 (c)(1),
(2) Date: Jan. 28, 2020

(87) PCT Pub. No.: WO2019/067113
PCT Pub. Date: Apr. 4, 2019

(65) Prior Publication Data
US 2020/0207727 A1    Jul. 2, 2020

Related U.S. Application Data

(60) Provisional application No. 62/564,538, filed on Sep. 28, 2017.

(51) Int. Cl.
C07D 265/32 (2006.01)
C07C 231/14 (2006.01)
C07D 207/24 (2006.01)

(52) U.S. Cl.
CPC .......... *C07D 265/32* (2013.01); *C07C 231/14* (2013.01); *C07D 207/24* (2013.01)

(58) Field of Classification Search
CPC .... C07D 207/24; C07D 265/38; C07C 231/24
See application file for complete search history.

(56) References Cited

U.S. PATENT DOCUMENTS

| | | | |
|---|---|---|---|
| 5,104,034 A | 4/1992 | Hansen | |
| 6,203,944 B1 | 3/2001 | Turner | |
| 6,255,017 B1 | 7/2001 | Turner | |
| 8,578,714 B2 * | 11/2013 | Nagurny | F03G 7/00 60/645 |
| 2010/0139274 A1 | 6/2010 | Zyhowski | |
| 2016/0145195 A1 | 5/2016 | Bulinski | |
| 2017/0198186 A1 | 7/2017 | Bulinski | |

OTHER PUBLICATIONS

Banks, "Fluorocarbon Derivatives of Nitrogen Part I Some Reactions of Perfluoro-1-Azacyclohexene", Journal of Fluorine Chemistry, Jul. 1978, vol. 12, No. 1, pp. 27-34.

Coe, "Highly Fluorinated Heterocycles Part XVII Chlorinations of 1-Methylpolyfluoro-pyrrolidines and Reactions of Derived Products" Journal of Fluorine Chemistry, Jun. 1983, vol. 22, No. 6, pp. 521-539.

Dias, "Silver(I) and Copper(I) Complexes Supported by Fully Fluorinated 1,3,5-Triazapentadienyl Ligands", Dalton Transaction, Sep. 2011, vol. 40, No. 34, pp. 8569-8580.

Ellis, Cleaning and Contamination of Electronics Components and Assemblies, 182-194 (1986).

Gontar, "Preparation of Internal Perfluoroazomethines and Generation of Fluoroazanions from them", Russian Chemical Bulletin (Translated from Izvestiya Akademii Nauk), Aug. 1984, vol. 33 No. 8, pp. 1711-1714.

Grinevskaja, "Reactivity of N-Perfluoromorpholynyl AZA-Anion", Fluorine Notes, Mar.-Apr. 2009, vol. 63, No. 2, 6 pages.

Hayashi, "The Reaction of Perfluoro (N-Alkyl-Cyclic Amines) with Oleum. The Formation and Characterization of Perfluorolactams" Journal of Fluorine Chemistry Nov. 1988, vol. 41, No. 2, pp. 213-225.

Krespan, "Fluoroalkyl Azide Chemistry" Journal of Organic Chemistry, Feb. 1986, vol. 51, No. 3, pp. 332-337.

Nishida, "Polyfluoroalkylation and Polyfluoroalkoxylation of Perfluoro-(5,6-dihydro-2H-1,4-oxazine) in the Presence of Fluoride Anion", Journal of Fluorine Chemistry, Aug. 1998, vol. 91, No. 1, pp. 1-3.

Nishida, "Reactions of Perfluorocycloimines with (Polyfluoroalkoxy)trimethylsilanes and Polyfluoroalkyltrifluoromethanesulfonates" Journal of Fluorine Chemistry, Jul. 2001, vol. 110, No. 1, pp. 63-73.

Pawelke, "Fluroination with Concomitant Cyclization of $CCl_2N=CCl_2CCl_2=NCCl_2$ with $SbF_5$ and Molecular Structure of a 2-Imidazolidinone Derivative", Journal of Fluorine Chemistry, Jul. 1987, vol. 36, No. 2, pp. 185-194.

Petrov, "Cleavage of Perfluorinated Tertiary Amines by Antimony Pentafluoride", Russian Chemical Bulletin (Translated from Izvestiya Akademii Nauk), Jan. 1989, vol. 38, No. 1, pp. 110-113.

(Continued)

*Primary Examiner* — John Mabry
(74) *Attorney, Agent, or Firm* — Julie Lapos-Kuchar

(57) ABSTRACT

Described herein is an hydrofluorocarboximidate of formula (I) where: $R_H$ is a linear or branched alkyl group comprising 1 or 2 carbon atoms and (a) $R_f1$ and $R_f2$ are independent-selected from a linear or branched perfluorinated alkyl group comprising 1-8 carbon atoms and optionally comprising at least one catenated atom selected from oxygen, nitrogen, or combinations thereof; or (b) $R_f1$ and $R_f2$ are connected to form a ring structure comprising a total of 4-8 carbon atoms and in addition to the nitrogen atom from the carboximidate the ring structure may optionally comprises at least one catenated atom selected from oxygen, nitrogen, or combinations thereof. A method of making the hydrofluorocarboximidate with improved yield is described as well as various uses for the hydrofluorocarboximidate of Formula (I).

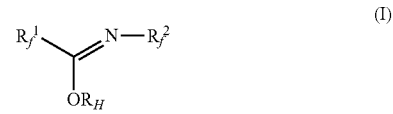

(I)

18 Claims, No Drawings

(56) References Cited

OTHER PUBLICATIONS

Petrov, "Reaction of Higher Perfluorinated Amines with Antimony Pentafluoride", Russian Chemical Bulletin (Translated from Izvestiya Akademii Nauk), Jan. 1985, vol. 34, No. 8, p. 1789.

Rogoza, "Reaction of Triethyl Phosphite with Internal Perfluoroolefins and Their Aza Analogs", Russian Journal of General Chemistry, May 1998, vol. 68, No. 5, pp. 753-760.

International Search Report for PCT International Application No. PCT/US2018/047621, dated Nov. 6, 2018, 5 pages.

* cited by examiner

HYDROFLUOROCARBOXIMIDATE AND METHODS OF MAKING AND USING THE SAME

CROSS REFERENCE TO RELATED APPLICATIONS

This application is a national stage filing under 35 U.S.C. 371 of PCT/US2018/047621, filed Aug. 23, 2018, which claims the benefit of U.S. Application No. 62/564,538, filed Sep. 28, 2017, the disclosure of which is incorporated by reference in its/their entirety herein.

TECHNICAL FIELD

The present disclosure relates to a hydrofluorocarboximidate and methods of making and using the same.

SUMMARY

There continues to be a need for inert fluorinated fluids which have low global warming potential while providing high thermal stability, low toxicity, nonflammability, good solvency, and a wide operating temperature range to meet the requirements of various applications. Those applications include, but are not restricted to, heat transfer, solvent cleaning, fire extinguishing agents, and electrolyte solvents and additives.

In one aspect, method of making of a hydrofluorocarboximidate is provided, the method comprising:
contacting a perfluorinated imine with a trialkyl borate in the presence of base to form hydrofluorocarboximidate of formula (I)

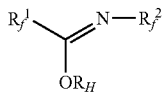

where:
$R_f^1$ and $R_f^2$ are independently selected from a linear or branched perfluorinated alkyl group comprising 1-8 carbon atoms and optionally comprising at least one catenated atom selected from O, N, S or combinations thereof, or $R_f^1$ and $R_f^2$ are connected in a ring structure comprising 4-8 carbon atoms; and $R_H$ is a linear or branched alkyl group comprising 1 or 3 carbon atoms.

The above summary is not intended to describe each embodiment. The details of one or more embodiments of the invention are also set forth in the description below. Other features, objects, and advantages will be apparent from the description and from the claims.

DETAILED DESCRIPTION

As used herein, the term
"a", "an", and "the" are used interchangeably and mean one or more; and
"and/or" is used to indicate one or both stated cases may occur, for example A and/or B includes, (A and B) and (A or B);
"alkyl" refers to a monovalent group that is a radical of an alkane, which is a saturated hydrocarbon. The alkyl group can be linear, branched, cyclic or combinations thereof;
"catenated" means an atom other than carbon (for example, oxygen or nitrogen) that is bonded to at least two carbon atoms in a carbon chain (linear or branched or within a ring) so as to form a carbon-heteroatom-carbon linkage; and
"perfluorinated" means a group or a compound wherein all hydrogen atoms in the C—H bonds have been replaced by C—F bonds.

As used herein, a chemical structure that depicts the letter "F" in the center of the ring indicated that all unmarked bonds of the ring are fluorine atoms.

Also herein, recitation of ranges by endpoints includes all numbers subsumed within that range (e.g., 1 to 10 includes 1.4, 1.9, 2.33, 5.75, 9.98, etc.).

Also herein, recitation of "at least one" includes all numbers of one and greater (e.g., at least 2, at least 4, at least 6, at least 8, at least 10, at least 25, at least 50, at least 100, etc.).

Heat transfer fluids may be used to transmit heat from one location to another, for example, to prevent over heating of a device or to maintain precise temperature control or for energy conversion, as in the capture of waste heat and the conversion to electrical or mechanical energy. Presently, various fluids are used for heat transfer. The suitability of the heat transfer fluid depends upon the application process. For example, in some electronic applications, a heat-transfer fluid which is inert, has low toxicity, good environmental properties, and good heat transfer properties over a wide temperature range is desirable.

In some embodiments, the hydrofluorocarboximidate of the present disclosure may exhibit properties that render them particularly useful as heat transfer fluids for the electronics industry. For example, the hydrofluorocarboximidate may be chemically inert (i.e., they do not easily react with base, acid, water, etc.), and may have high boiling points (up to 300° C.), low freezing points (the hydrofluorocarboximidate may be liquid at −40° C. or lower), low viscosity, high thermal stability, good thermal conductivity, adequate solvency for a range of potentially important solutes, and low toxicity. The hydrofluorocarboximidate of the present disclosure may also, surprisingly, be liquid at room temperature (e.g., between 20 and 25° C.).

Further, in one embodiment, the compounds of the present disclosure can be readily prepared in high yield via low cost starting materials. The starting materials can be readily purchased or derived from synthesis. Thus, the hydrofluorocarboximidates described in the present disclosure may be a potentially low cost fluorinated fluid that can be used in heat transfer, cleaning, and electrolyte applications.

The hydrofluorocarboximidate of the present disclosure (herein referred to interchangeably as a compound of the present disclosure) are of the general formula (I)

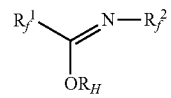

where:
$R_H$ is a linear or branched alkyl group comprising 1 or 2 carbon atoms and (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and in addition to the nitrogen atom from the carboximidate the ring structure may optionally comprises at least one catenated atom selected from oxygen, nitrogen, or combinations thereof.

In one embodiment, $R_H$ is —CH$_3$, or —CH$_2$CH$_3$.

In one embodiment, $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof. Exemplary $R_f^1$ and $R_f^2$ groups include: —CF$_3$; —(CF$_2$)$_n$CF$_3$ where n is 1, 2, 3, 4, 5, or 6; and —CF$_2$CF(CF$_3$)CF$_2$CF$_3$.

In one embodiment, $R_f^1$ and $R_f^2$ are connected to form a ring structure moiety comprising a total of 4-8 carbon atoms in additional to optional catenary heteroatoms such as oxygen or nitrogen. The ring structure moiety may comprise a 4-, 5-, or 6-membered ring. The ring which is made up of the nitrogen atom from the carboximidate may also include an oxygen or nitrogen atom in the ring. In addition, or alternatively, the ring may comprise pendent perfluorinated alkyl groups, which may optionally comprise at least one catenated atom selected from oxygen, nitrogen, or combinations thereof. Exemplary ringed structures include: 5-membered rings such as pyrroles, and 6-membered rings such pyridines, and six membered rings comprising a catenated oxygen (such as 1, 4-ozazines) or catenated nitrogen (such as piperazines).

Exemplary compounds of the present disclosure include:

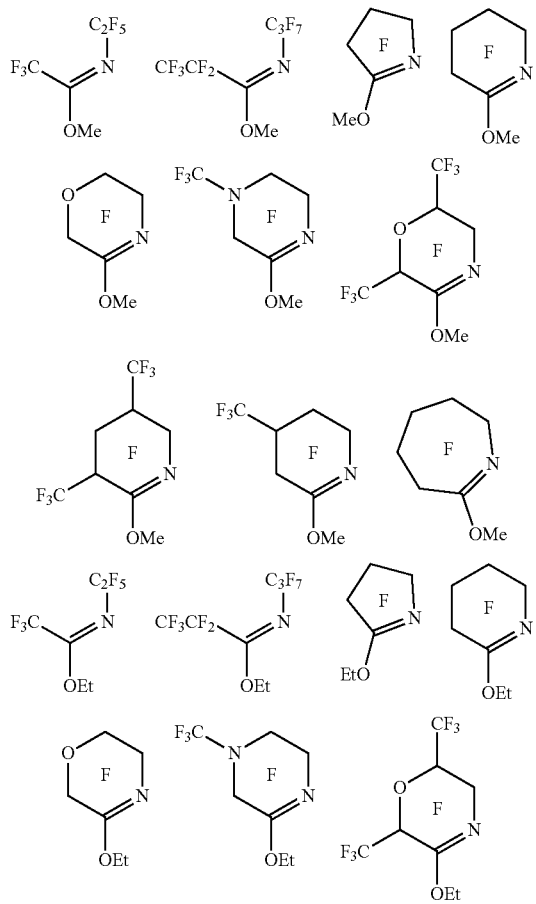

-continued

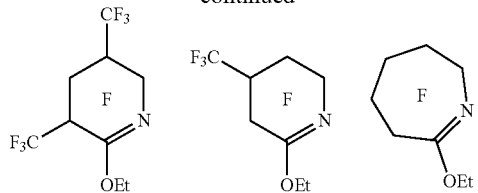

wherein Me refers to a —CH$_3$ and Et refers to a —CH$_2$CH$_3$.

The compounds of the present disclosure have good environmental properties as well as having good performance attributes, such as non-flammability, chemical inertness, high thermal stability, good solvency, etc.

In one embodiment, the compound of the present disclosure is thermally stable, meaning that when the compound is heated, there is minimal loss of purity. For example, if the hydrofluorocarboximidate is heated at 50° C. for 24 hours, there is a loss of less than 5%, or even 1%.

In one embodiment, the compound of the present disclosure may have a low environmental impact. In this regard, the compounds of the present disclosure may have a global warming potential (GWP) of less than 500, 400, 300, 200, or even 100. As used herein, GWP is a relative measure of the global warming potential of a compound based on the structure of the compound. The GWP of a compound, as defined by the Intergovernmental Panel on Climate Change (IPCC) in 1990 and updated in 2007, is calculated as the warming due to the release of 1 kilogram of a compound relative to the warming due to the release of 1 kilogram of CO$_2$ over a specified integration time horizon (ITH).

$$GWP_i(t') = \frac{\int_0^{ITH} a_i[C(t)]dt}{\int_0^{ITH} a_{CO_2}[C_{CO_2}(t)]dt} = \frac{\int_0^{ITH} a_i C_{oi} e^{-t/\tau_i} dt}{\int_0^{ITH} a_{CO_2}[C_{CO_2}(t)]dt}$$

In this equation $a_i$ is the radiative forcing per unit mass increase of a compound in the atmosphere (the change in the flux of radiation through the atmosphere due to the IR absorbance of that compound), C is the atmospheric concentration of a compound, τ is the atmospheric lifetime of a compound, t is time, and i is the compound of interest. The commonly accepted ITH is 100 years representing a compromise between short-term effects (20 years) and longer-term effects (500 years or longer). The concentration of an organic compound, i, in the atmosphere is assumed to follow pseudo first order kinetics (i.e., exponential decay). The concentration of CO$_2$ over that same time interval incorporates a more complex model for the exchange and removal of CO$_2$ from the atmosphere (the Bern carbon cycle model).

In one embodiment, the compounds of the present disclosure have atmospheric lifetime of less than 1 year, or even less than 0.5 years.

Non-flammability can be assessed by using standard methods such as ASTM D-3278-96 e-1"Standard Test Method for Flash Point of Liquids by Small Scale Closed-Cup Apparatus". In one embodiment, the compound of the present disclosure is non-flammable based on closed-cup flashpoint testing following ASTM D-3278-96 e-1.

In one embodiment, the compound of the present disclosure is non-bioaccumulative in animal tissues. For example, some compounds of the present disclosure may provide low log $K_{ow}$ values, indicating a reduced tendency to bioaccumulate in animal tissues, where $K_{ow}$ is the octanol/water partition coefficient, which is defined as the ratio of the given compound's concentration in a two-phase system comprising an octanol phase and an aqueous phase. In one embodiment, the log $K_{ow}$ value is less than 7, 6, 5, or even 4.

The useful liquid range of a compound of the present disclosure is between its pour point and its boiling point. A pour point is the lowest temperature at which the compound is still able to be poured. The pour point can be determined, for example, by ASTM D 97-16 "Standard Test Method for Pour Point of Petroleum Products". In one embodiment, the compound of the present disclosure has a pour point of less than 0° C., −20° C., −40° C. or even −60° C. In one embodiment, the compound of the present disclosure has a boiling point of at least 100° C., 150° C., or even 200° C.

In some embodiments, the compound of the present disclosure may be hydrophobic, relatively chemically unreactive, and thermally stable.

Herein methods of making and using the hydrofluorocarboximidates are disclosed.

In one embodiment, the compound of the present disclosure can be prepared by the nucleophilic substitution of a perfluorinated imine by an alcohol (such as methanol or ethanol) in the presence of a base (such as potassium carbonate). However, the reaction yields for the hydrofluorocarboximidate of formula (I) tend to be low (e.g., less than 65%, 50%, or even 30% of the desired product) due to poor selectivity.

In the present disclosure, it has been discovered that if the perfluorinated imine is reacted in the presence of a trialkyl borate and a base, improved reaction yields can be obtained. For example, reaction yields greater than 75, 80, or even 90% of the desired product.

In one embodiment, the perfluorinated imine is selected from a perfluorinated imidoyl fluoride, a perfluorinated oxazine, or a perfluorinated pyrrole compound. Such compounds are commercially available or can be synthesized using methods such as those disclosed in H. V. Rasika Dias et al. in Dalton Transactions, 2011, vol. 40, page 8569-8580; V. K. Grinevskaja, et al. in Fluorine Notes, 2009, volume 2 (63); and A. F. Gontar, et al. in Izvestiya Akademii Nauk SSSR, Seriya Khimicheskaya 1984, vol. 33 issue 8, pages 1711-1714.

Exemplary perfluorinated imines include:

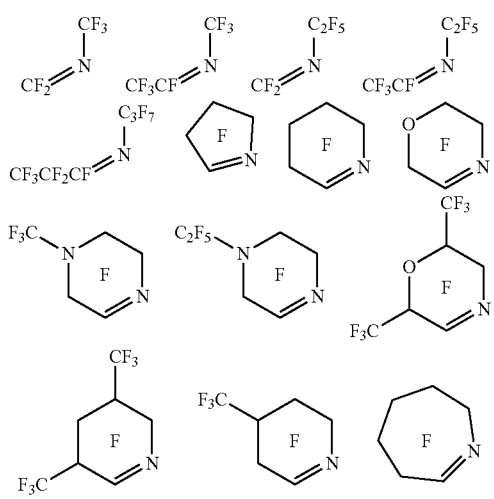

In one embodiment, the trialkyl borate comprises an alkyl group comprising a methyl and/or an ethyl moiety. Exemplary trialkyl borates include trimethylborate and triethylborate. When the alkyl group is larger than 3 carbons, the resulting carboximidate is thought to be more flammable and thus, not desired for the applications disclosed herein.

The trialkyl borate and the perfluorinated imine are reacted in the presence of a base. Exemplary bases include carbonates such as sodium bicarbonate, potassium bicarbonate, sodium carbonate, or potassium carbonate.

The trialkyl borate and the perfluorinated imine are combined in the presence of the base and heated, whether it is to ambient temperature or higher temperatures such as temperatures greater than 40, 50, or 70° C.

In one embodiment, the resulting fluorinated compounds can be purified to isolate the desired hydrofluorocarboximidate. Purification can be done by conventional means including distillation, absorption, extraction, chromatography and recrystallization. The purification can be done to isolate the compound of the present disclosure (in all of its stereoisomeric forms) from impurities, such as starting materials, byproducts, etc. The term "purified form" as used herein means the compound of the present disclosure is at least 75, 80, 85, 90, 95, 98, or even 99 wt % pure.

The compounds of the present disclosure may be used as a working fluid in a variety of applications. The working fluids may include at least 25%, 50%, 70%, 80%, 90%, 95%, 99%, or even 100% by weight of the above-described formula (I) compounds based on the total weight of the working fluid. In addition to the compounds of the present disclosure, the working fluids may include a total of up to 75%, up to 50%, up to 30%, up to 20%, up to 10%, or up to 5% by weight of one or more of the following components: alcohols, ethers, alkanes, alkenes, haloalkenes, perfluorocarbons, perfluorinated tertiary amines, perfluoroethers, cycloalkanes, esters, ketones, oxiranes, aromatics, siloxanes, unsaturated hydrochlorocarbons, unsaturated hydrochlorofluorocarbons, unsaturated hydrofluorocarbons, non-hetero atom-containing hydrofluoroolefins, hydrochloroolefins, hydrochlorofluoroolefins, unsaturated hydrofluoroethers, or mixtures thereof, based on the total weight of the working fluid. Such additional components can be chosen to modify or enhance the properties of a composition for a particular use.

In one embodiment, the working fluid has no flash point (as measured, for example, following ASTM D-3278-96 e-1).

In one embodiment, the compound of the present disclosure may be used in an apparatus for heat transfer that includes a device and a mechanism for transferring heat to or from the device. The mechanism for transferring heat may include a heat transfer working fluid that includes a compound of formula (I) of the present disclosure.

The provided apparatus for heat transfer may include a device. The device may be a component, work-piece, assembly, etc. to be cooled, heated or maintained at a predetermined temperature or temperature range. Such devices include electrical components, mechanical components and optical components. Examples of devices of the present disclosure include, but are not limited to microprocessors, wafers used to manufacture semiconductor devices, power control semiconductors, electrical distribution switch gear, power transformers, circuit boards, multi-chip modules, packaged and unpackaged semiconductor devices, lasers, chemical reactors, fuel cells, and electrochemical cells. In some embodiments, the device can include a chiller, a heater, or a combination thereof.

In yet other embodiments, the devices can include electronic devices, such as processors, including microprocessors. As these electronic devices become more powerful, the amount of heat generated per unit time increases. Therefore, the mechanism of heat transfer plays an important role in processor performance. The heat-transfer fluid typically has good heat transfer performance, good electrical compatibility (even if used in "indirect contact" applications such as those employing cold plates), as well as low toxicity, low (or non-) flammability and low environmental impact. Good electrical compatibility suggests that the heat-transfer fluid candidate exhibit high dielectric strength, high volume resistivity, and poor solvency for polar materials. Additionally, the heat-transfer fluid should exhibit good mechanical compatibility, that is, it should not affect typical materials of construction in an adverse manner.

The provided apparatus may include a mechanism for transferring heat. The mechanism may include a heat transfer fluid. The heat transfer fluid may include one or more compounds of the present disclosure. Heat may be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism.

The heat transfer mechanism may include facilities for managing the heat-transfer fluid, including, but not limited to pumps, valves, fluid containment systems, pressure control systems, condensers, heat exchangers, heat sources, heat sinks, refrigeration systems, active temperature control systems, and passive temperature control systems. Examples of suitable heat transfer mechanisms include, but are not limited to, temperature controlled wafer chucks in plasma enhanced chemical vapor deposition (PECVD) tools, temperature-controlled test heads for die performance testing, temperature-controlled work zones within semiconductor process equipment, thermal shock test bath liquid reservoirs, and constant temperature baths. In some systems, such as etchers, ashers, PECVD chambers, vapor phase soldering devices, and thermal shock testers, the upper desired operating temperature may be as high as 170° C., as high as 200° C., or even as high as 230° C.

Heat can be transferred by placing the heat transfer mechanism in thermal contact with the device. The heat transfer mechanism, when placed in thermal contact with the device, removes heat from the device or provides heat to the device, or maintains the device at a selected temperature or temperature range. The direction of heat flow (from device or to device) is determined by the relative temperature difference between the device and the heat transfer mechanism. The provided apparatus can also include refrigeration systems, cooling systems, testing equipment and machining equipment. In some embodiments, the provided apparatus can be a constant temperature bath or a thermal shock test bath. In some systems, such as etchers, ashers, PECVD chambers, vapor phase soldering devices, and thermal shock testers, the upper desired operating temperature may be as high as 170° C., as high as 200° C., 250 C or even higher.

In some embodiments, the compounds of the present disclosure may be used as a heat transfer agent for use in vapor phase soldering. In using the compounds of the present disclosure in vapor phase soldering, the process described in, for example, U.S. Pat. No. 5,104,034 (Hansen) can be used, which description is hereby incorporated by reference. Briefly, such process includes immersing a component to be soldered in a body of vapor comprising at least an hydrofluorocarboximidate of the present disclosure to melt the solder. In carrying out such a process, a liquid pool of the hydrofluorocarboximidate (or working fluid that includes the acyclic fluorinated compound) is heated to boiling in a tank to form a saturated vapor in the space between the boiling liquid and a condensing means.

A workpiece to be soldered is immersed in the vapor (at a temperature of greater than 170° C., greater than 200° C., greater than 230° C., 250 C, or even greater), whereby the vapor is condensed on the surface of the workpiece so as to melt and reflow the solder. Finally, the soldered workpiece is then removed from the space containing the vapor.

In another embodiment, the compound of the present disclosure is used in an apparatus for converting thermal energy into mechanical energy in a Rankine cycle. The apparatus may include a working fluid that includes one or more compounds of formula (I). The apparatus may further include a heat source to vaporize the working fluid and form a vaporized working fluid, a turbine through which the vaporized working fluid is passed thereby converting thermal energy into mechanical energy, a condenser to cool the vaporized working fluid after it is passed through the turbine, and a pump to recirculate the working fluid.

In some embodiments, the present disclosure relates to a process for converting thermal energy into mechanical energy in a Rankine cycle. The process may include using a heat source to vaporize a working fluid that includes one or more compounds of formula (I) to form a vaporized working fluid. In some embodiments, the heat is transferred from the heat source to the working fluid in an evaporator or boiler. The vaporized working fluid may pressurized and can be used to do work by expansion. The heat source can be of any form such as from fossil fuels, e.g., oil, coal, or natural gas. Additionally, in some embodiments, the heat source can come from nuclear power, solar power, or fuel cells. In other embodiments, the heat can be "waste heat" from other heat transfer systems that would otherwise be lost to the atmosphere. The "waste heat," in some embodiments, can be heat that is recovered from a second Rankine cycle system from the condenser or other cooling device in the second Rankine cycle.

An additional source of "waste heat" can be found at landfills where methane gas is flared off. In order to prevent methane gas from entering the environment and thus contributing to global warming, the methane gas generated by the landfills can be burned by way of "flares" producing carbon dioxide and water which are both less harmful to the environment in terms of global warming potential than methane. Other sources of "waste heat" that can be useful in the provided processes are geothermal sources and heat from other types of engines such as gas turbine engines that give off significant heat in their exhaust gases and to cooling liquids such as water and lubricants.

In the provided process, the vaporized working fluid may expanded though a device that can convert the pressurized working fluid into mechanical energy. In some embodiments, the vaporized working fluid is expanded through a turbine which can cause a shaft to rotate from the pressure of the vaporized working fluid expanding. The turbine can then be used to do mechanical work such as, in some embodiments, operate a generator, thus generating electricity. In other embodiments, the turbine can be used to drive belts, wheels, gears, or other devices that can transfer mechanical work or energy for use in attached or linked devices.

After the vaporized working fluid has been converted to mechanical energy the vaporized (and now expanded) working fluid can be condensed using a cooling source to liquefy for reuse. The heat released by the condenser can be used for other purposes including being recycled into the same or another Rankine cycle system, thus saving energy. Finally, the condensed working fluid can be pumped by way of a pump back into the boiler or evaporator for reuse in a closed system.

The desired thermodynamic characteristics of organic Rankine cycle working fluids are well known to those of ordinary skill and are discussed, for example, in U.S. Pat. Appl. Publ. No. 2010/0139274 (Zyhowski et al.). The greater the difference between the temperature of the heat source and the temperature of the condensed liquid or a provided heat sink after condensation, the higher the Rankine cycle thermodynamic efficiency. The thermodynamic efficiency is influenced by matching the working fluid to the heat source temperature. The closer the evaporating temperature of the working fluid to the source temperature, the higher the efficiency of the system. Toluene can be used, for example, in the temperature range of 79° C. to about 260° C., however toluene has toxicological and flammability concerns. Fluids such as 1,1-dichloro-2,2,2-trifluoroethane and 1,1,1,3,3-pentafluoropropane can be used in this temperature range as an alternative. But 1,1-dichloro-2,2,2-trifluoroethane can form toxic compounds below 300° C. and need to be limited to an evaporating temperature of about 93° C. to about 121° C. Thus, there is a desire for other environmentally-friendly Rankine cycle working fluids with higher critical temperatures so that source temperatures such as gas turbine and internal combustion engine exhaust can be better matched to the working fluid.

In one embodiment, the compound of the present disclosure is used in a cleaning compositions along with one or more co-solvents. In some embodiments, the present disclosure relates to a process for cleaning a substrate. The cleaning process can be carried out by contacting a contaminated substrate with a cleaning composition. The compound of the present disclosure can be utilized alone or in admixture with each other or with other commonly-used cleaning co-solvents. Representative examples of co-solvents which can be used in the cleaning composition include methanol, ethanol, isopropanol, t-butyl alcohol, methyl t-butyl ether, methyl t-amyl ether, 1,2-dimethoxyethane, cyclohexane, 2,2,4-trimethylpentane, n-decane, terpenes (e.g., a-pinene, camphene, and limonene), trans-1,2-dichloroethylene, cis-1,2-dichloroethylene, methylcyclopentane, decalin, methyl decanoate, t-butyl acetate, ethyl acetate, diethyl phthalate, 2-butanone, methyl isobutyl ketone, naphthalene, toluene, p-chlorobenzotrifluoride, trifluorotoluene, bis(trifluoromethyl)benzenes, hexamethyl disiloxane, octamethyl trisiloxane, perfluorohexane, perfluoroheptane, perfluorooctane, perfluorotributylamine, perfluoro-N-methyl morpholine, perfluoro-2-butyl oxacyclopentane, methylene chloride, chlorocyclohexane, 1-chlorobutane, 1,1-dichloro-1-fluoroethane, 1,1,1-trifluoro-2,2-dichloroethane, 1,1,1,2,2-pentafluoro-3,3-dichloropropane, 1,1,2,2,3-pentafluoro-1,3-dichloropropane, 2,3-dihydroperfluoropentane, 1,1,1,2,2,4-hexafluorobutane, 1-trifluoromethyl-1,2,2-trifluorocyclobutane, 3-methyl-1,1,2,2-tetrafluorocyclobutane, 1-hydropentadecafluoroheptane, or mixtures thereof. Such co-solvents can be chosen to modify or enhance the solvency properties of a cleaning composition for a particular use and can be utilized in ratios (of co-solvent to compounds according to formula (I)) such that the resulting composition has no flash point. If desirable for a particular application, the cleaning composition can further contain one or more dissolved or dispersed gaseous, liquid, or solid additives (for example, carbon dioxide gas, surfactants, stabilizers, antioxidants, or activated carbon).

In some embodiments, the present disclosure relates to cleaning compositions that include one or more compounds of the present disclosure and optionally one or more surfactants. Suitable surfactants include those surfactants that are sufficiently soluble in the compound of the present disclosure, and which promote soil removal by dissolving, dispersing or displacing the soil. One useful class of surfactants are those nonionic surfactants that have a hydrophilic-lipophilic balance (HLB) value of less than about 14. Examples include ethoxylated alcohols, ethoxylated alkylphenols, ethoxylated fatty acids, alkylaryl sulfonates, glycerol esters, ethoxylated fluoroalcohols, and fluorinated sulfonamides. Mixtures of surfactants having complementary properties may be used in which one surfactant is added to the cleaning composition to promote oily soil removal and another added to promote water-soluble soil removal. The surfactant, if used, can be added in an amount sufficient to promote soil removal. Typically, surfactant may be added in amounts from 0.1 to 5.0 wt. % or from 0.2 to 2.0 wt. % of the cleaning composition.

The cleaning compositions can be used in either the gaseous or the liquid state (or both), and any of known or future techniques for "contacting" a substrate can be utilized. For example, a liquid cleaning composition can be sprayed or brushed onto the substrate, a gaseous cleaning composition can be blown across the substrate, or the substrate can be immersed in either a gaseous or a liquid composition. Elevated temperatures, ultrasonic energy, and/or agitation can be used to facilitate the cleaning. Various different solvent cleaning techniques are described by B. N. Ellis in *Cleaning and Contamination of Electronics Components and Assemblies*, Electrochemical Publications Limited, Ayr, Scotland, pages 182-94 (1986).

Both organic and inorganic substrates can be cleaned by the processes of the present disclosure. Representative examples of the substrates include metals; ceramics; glass; polycarbonate; polystyrene; acrylonitrile-butadiene-styrene copolymer; natural fibers (and fabrics derived therefrom) such as cotton, silk, fur, suede, leather, linen, and wool; synthetic fibers (and fabrics) such as polyester, rayon, acrylics, nylon, or blends thereof; fabrics comprising a blend of natural and synthetic fibers; and composites of the foregoing materials. In some embodiments, the process may be used in the precision cleaning of electronic components (e.g., circuit boards), optical or magnetic media, or medical devices.

In still another embodiment, the compound of the present disclosure is used in a dielectric fluids, which can be used in electrical devices (e.g., capacitors, switchgear, transformers, or electric cables or buses). For purposes of the present application, the term "dielectric fluid" is inclusive of both liquid dielectrics and gaseous dielectrics. The physical state of the fluid, gaseous or liquid, is determined at the operating conditions of temperature and pressure of the electrical device in which it is used.

In some embodiments, the dielectric fluids include one or more compounds of formula (I) and, optionally, one or more second dielectric fluids. Suitable second dielectric fluids include, for example, air, nitrogen, helium, argon, and carbon dioxide, or combinations thereof. The second dielectric fluid may be a non-condensable gas or an inert gas. Generally, the second dielectric fluid may be used in amounts such that vapor pressure is at least 70 kPa at 25° C., or at the operating temperature of the electrical device.

The dielectric fluids of the present application comprising the compounds of formula (I) are useful for electrical insulation and for arc quenching and current interruption equipment used in the transmission and distribution of electrical energy. Generally, there are three major types of electrical devices in which the fluids of the present disclosure can be used: (1) gas-insulated circuit breakers and current-interruption equipment, (2) gas-insulated transmission lines, and (3) gas-insulated transformers. Such gas-insulated equipment is a major component of power transmission and distribution systems.

In some embodiments, the present disclosure provides electrical devices, such as capacitors, comprising metal electrodes spaced from each other such that the gaseous dielectric fills the space between the electrodes. The interior space of the electrical device may also comprise a reservoir of the liquid dielectric fluid which is in equilibrium with the gaseous dielectric fluid. Thus, the reservoir may replenish any losses of the dielectric fluid.

In another embodiment, the present disclosure relates to coating compositions comprising (a) a solvent composition that includes one or more compounds of the present disclosure, and (b) one or more coating materials which are soluble or dispersible in the solvent composition.

In various embodiments, the coating materials of the coating compositions may include pigments, lubricants, stabilizers, adhesives, anti-oxidants, dyes, polymers, pharmaceuticals, release agents, inorganic oxides, and the like, and combinations thereof. For example, coating materials may include unsaturated perfluoropolyether, unsaturated hydrocarbon, and silicone lubricants; amorphous copolymers of tetrafluoroethylene; polytetrafluoroethylene; or combinations thereof. Further examples of suitable coating materials include titanium dioxide, iron oxides, magnesium oxide, unsaturated perfluoropolyethers, polysiloxanes, stearic acid, acrylic adhesives, polytetrafluoroethylene, amorphous copolymers of tetrafluoroethylene, or combinations thereof.

In some embodiments, the above-described coating compositions can be useful in coating deposition, where the compounds of Formula (I) function as a carrier for a coating material to enable deposition of the material on the surface of a substrate. In this regard, the present disclosure further relates to a process for depositing a coating on a substrate surface using the coating composition. The process comprises the step of applying to at least a portion of at least one surface of a substrate a coating of a liquid coating composition comprising (a) a solvent composition containing one or more of the compounds of formula (I); and (b) one or more coating materials which are soluble or dispersible in the solvent composition. The solvent composition can further comprise one or more co-dispersants or co-solvents and/or one or more additives (e.g., surfactants, coloring agents, stabilizers, anti-oxidants, flame retardants, and the like). Preferably, the process further comprises the step of removing the solvent composition from the coating by, e.g., allowing evaporation (which can be aided by the application of, e.g., heat or vacuum).

In various embodiments, to form a coating composition, the components of the coating composition (i.e., the compound(s) of formula (I), the coating material(s), and any co-dispersant(s) or co-solvent(s) utilized) can be combined by any conventional mixing technique used for dissolving, dispersing, or emulsifying coating materials, e.g., by mechanical agitation, ultrasonic agitation, manual agitation, and the like. The solvent composition and the coating material(s) can be combined in any ratio depending upon the desired thickness of the coating. For example, the coating material(s) may constitute from about 0.1 to about 10 weight percent of the coating composition.

In illustrative embodiments, the deposition process of the disclosure can be carried out by applying the coating composition to a substrate by any conventional technique. For example, the composition can be brushed or sprayed (e.g., as an aerosol) onto the substrate, or the substrate can be spin-coated. In some embodiments, the substrate may be coated by immersion in the composition. Immersion can be carried out at any suitable temperature and can be maintained for any convenient length of time. If the substrate is a tubing, such as a catheter, and it is desired to ensure that the composition coats the lumen wall, the composition may be drawn into the lumen by the application of reduced pressure.

In various embodiments, after a coating is applied to a substrate, the solvent composition can be removed from the coating (e.g., by evaporation). If desired, the rate of evaporation can be accelerated by application of reduced pressure or mild heat. The coating can be of any convenient thickness, and, in practice, the thickness will be determined by such factors as the viscosity of the coating material, the temperature at which the coating is applied, and the rate of withdrawal (if immersion is utilized).

Both organic and inorganic substrates can be coated by the processes of the present disclosure. Representative examples of the substrates include metals, ceramics, glass, polycarbonate, polystyrene, acrylonitrile-butadiene-styrene copolymer, natural fibers (and fabrics derived therefrom) such as cotton, silk, fur, suede, leather, linen, and wool, synthetic fibers (and fabrics) such as polyester, rayon, acrylics, nylon, or blends thereof, fabrics including a blend of natural and synthetic fibers, and composites of the foregoing materials. In some embodiments, substrates that may be coated include, for example, magnetic hard disks or electrical connectors with perfluoropolyether lubricants or medical devices with silicone lubricants.

In some embodiments, the present disclosure further relates to electrolyte compositions that include one or more compounds of the present disclosure. The electrolyte compositions may comprise (a) a solvent composition including one or more of the compounds according to formula (I); and (b) at least one electrolyte salt. The electrolyte compositions of the present disclosure exhibit excellent oxidative stability, and when used in high voltage electrochemical cells (such as rechargeable lithium ion batteries) provide outstanding cycle life and calendar life. For example, when such electrolyte compositions are used in an electrochemical cell with a graphitized carbon electrode, the electrolytes provide stable cycling to a maximum charge voltage of at least 4.5V and up to 6.0V vs. Li/Li$^+$.

Electrolyte salts that are suitable for use in preparing the electrolyte compositions of the present disclosure include those salts that comprise at least one cation and at least one weakly coordinating anion (the conjugate acid of the anion having an acidity greater than or equal to that of a hydrocarbon sulfonic acid (for example, $PF_6^-$ anion or a bis (perfluoroalkanesulfonyl)imide anion); that are at least partially soluble in a selected compound of formula (I) (or in a blend thereof with one or more other compounds of formula (I) or one or more conventional electrolyte solvents); and that at least partially dissociate to form a conductive electrolyte composition. The salts may be stable over a range of operating voltages, are non-corrosive, and may be thermally and hydrolytically stable. Suitable cations include alkali metal, alkaline earth metal, Group IIB metal, Group IIIB metal, transition metal, rare earth metal, and ammonium (for example, tetraalkylammonium or trialkylammonium) cations, as well as a proton. In some embodiments, cations for battery use include alkali metal and alkaline earth metal cations. Suitable anions include fluorine-containing inorganic anions such as $(FSO_2)_2N^-$, $BF_4^-$, $PF_6^-$, $AsF_6^-$, and $SbF_6^-$; $ClO_4^-$; $HSO_4^-$; $H_2PO_4^-$; organic anions such as alkane, aryl, and alkaryl sulfonates; fluorine-containing and nonfluorinated tetraarylborates; carboranes and halogen-, alkyl-, or haloalkylsubstituted carborane anions including metallocarborane anions; and fluorine-containing organic anions such as perfluoroalkanesulfonates, cyanoperfluoroalkanesulfonylamides, bis(cyano)perfluoroalkanesulfonylmethides, (perfluoroalkanesulfonyl)imides, bis(perfluoroalkanesulfonyl)methides, and tris(perfluoroalkanesulfonyl)methides; and the like. Preferred anions for battery use include fluorine-containing inorganic anions (for example, $(FSO_2)_2N^-$, $BF_4^-$, $PF_6^-$, and $AsF_6^-$) and fluorine-containing organic anions (for example, perfluoroalkanesulfonates, bis(perfluoroalkanesulfonyl)imides, and tris(perfluoroalkanesulfonyl)methides). The fluorine-containing organic anions can be either fully fluorinated, that is perfluorinated, or partially fluorinated (within the organic portion thereof). In some embodiments, the fluorine-containing organic anion is at least about 80 percent fluorinated (that is, at least about 80 percent of the carbon-bonded substituents of the anion are fluorine atoms). In some embodiments, the anion is perfluorinated. The anions, including the perfluorinated anions, can contain one or more catenary heteroatoms such as, for example, nitrogen, oxygen, or sulfur. In some embodiments, fluorine-containing organic anions include perfluoroalkanesulfonates, bis(perfluoroalkanesulfonyl)imides, and tris(perfluoroalkanesulfonyl)methides.

In some embodiments, the electrolyte salts may include lithium salts. Suitable lithium salts include, for example, lithium hexafluorophosphate, lithium bis(trifluoromethanesulfonyl)imide, lithium bis(perfluoroethanesulfonyl)imide, lithium tetrafluoroborate, lithium perchlorate, lithium hexafluoroarsenate, lithium trifluoromethanesulfonate, lithium tris(trifluoromethanesulfonyl)methide, lithium bis(fluorosulfonyl)imide (Li—FSI), and mixtures of two or more thereof.

The electrolyte compositions of the present disclosure can be prepared by combining at least one electrolyte salt and a solvent composition including at least one compound of formula (I), such that the salt is at least partially dissolved in the solvent composition at the desired operating temperature. The compounds of the present disclosure (or a normally liquid composition including, consisting, or consisting essentially thereof) can be used in such preparation.

In some embodiments, the electrolyte salt is employed in the electrolyte composition at a concentration such that the conductivity of the electrolyte composition is at or near its maximum value (typically, for example, at a Li molar concentration of around 0.1-4.0 M, or 1.0-2.0 M, for electrolytes for lithium batteries), although a wide range of other concentrations may also be employed.

In some embodiments, one or more conventional electrolyte solvents are mixed with the compound(s) of formula (I) (for example, such that the compound(s) of formula (I) constitute from about 1 to about 80 or 90 percent of the resulting solvent composition). Useful conventional electrolyte solvents include, for example, organic and fluorine-containing electrolyte solvents (for example, propylene carbonate, ethylene carbonate, dimethyl carbonate, diethyl carbonate, ethyl methyl carbonate, dimethoxyethane, 7-butyrolactone, diglyme (that is, diethylene glycol dimethyl ether), tetraglyme (that is, tetraethylene glycol dimethyl ether), monofluoroethylene carbonate, vinylene carbonate, ethyl acetate, methyl butyrate, tetrahydrofuran, alkyl-substituted tetrahydrofuran, 1, 3-dioxolane, alkyl-substituted 1, 3-dioxolane, tetrahydropyran, alkyl-substituted tetrahydropyran, and the like, and mixtures thereof). Other conventional electrolyte additives (for example, a surfactant) can also be present, if desired.

The present disclosure further relates to electrochemical cells (e.g., fuel cells, batteries, capacitors, electrochromic windows) that include the above-described electrolyte compositions. Such an electrochemical cell may include a positive electrode, a negative electrode, a separator, and the above-described electrolyte composition.

A variety of negative and positive electrodes may be employed in the electrochemical cells. Representative negative electrodes include graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads); $Li_{4/3}Ti_{5/3}O_4$ the lithium alloy compositions described in U.S. Pat. No. 6,203,944 (Turner et al.) and U.S. Pat. No. 6,255,017 (Turner); and combinations thereof. Representative positive electrodes include $LiFePO_4$, $LiMnPO_4$, $LiCoPO_4$, $LiMn_2O_4$, $LiCoO_2$ and combinations thereof. The negative or positive electrode may contain additives such as will be familiar to those skilled in the art, e.g., carbon black for negative electrodes and carbon black, flake graphite and the like for positive electrodes.

The electrochemical devices of the present disclosure can be used in various electronic articles such as computers, power tools, automobiles, telecommunication devices, and the like.

Exemplary embodiment of the present disclosure include, but should not be limited to the following.

Embodiment 1. A method of making of a hydrofluorocarboximidate comprising:
contacting a perfluorinated imine with a trialkyl borate in the presence of base to form a hydrofluorocarboximidate of formula (I)

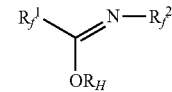

where:
$R_H$ is a linear or branched alkyl group comprising 1 or 2 carbon atoms; and
(a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 2. The method of embodiment 1, wherein $R_f^1$ and $R_f^2$ form a perfluorinated 6-membered ring, wherein the ring comprises an oxygen atom.

Embodiment 3. The method of embodiment 1, wherein ($R_f^1$) and $R_f$2 form a perfluorinated 5-membered ring.

Embodiment 4. The method of embodiment 1, wherein $R_f^1$ is a perfluoro ethyl group and $R_f^2$ is a perfluoro propyl group.

Embodiment 5. The method of any one of the previous embodiments, wherein $R_H$ is a methyl group.

Embodiment 6. The method of any one of embodiments 1-5, wherein $R_H$ is an ethyl group.

Embodiment 7. The method of any one of the previous embodiments, wherein the hydrofluorocarboximidate is selected from:

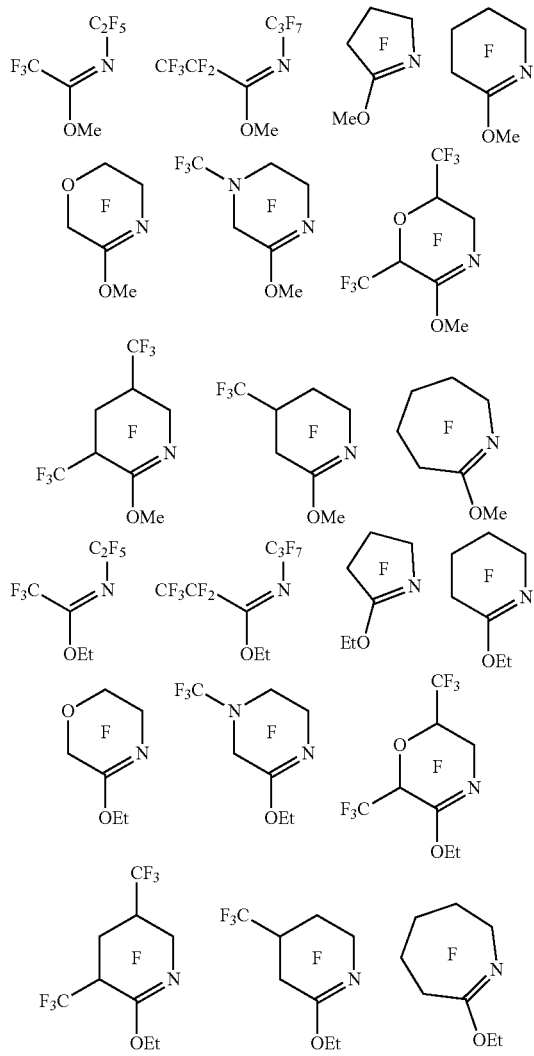

Embodiment 8. The method of any one of the previous embodiments, wherein the hydrofluorocarboximidate based on closed-cup flashpoint testing following ASTM D-327-96 e-1 is not flammable.

Embodiment 9. The method of any one of the previous embodiments, wherein the hydrofluorocarboximidate has a global warming potential of less than 100.

Embodiment 10. The method of any one of the previous embodiments, wherein the hydrofluorocarboximidate has a boiling point of 80 to 150 C.

Embodiment 11. A working fluid comprising a hydrofluorocarboximidate wherein the hydrofluorocarboximidate is present in the working fluid in an amount of at least 25% by weight based on the total weight of the working fluid and the hydrofluorocarboximidate is of formula (I)

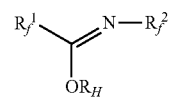

where:

$R_H$ is a linear or branched alkyl group comprising 1 or 2 carbon atoms; and (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 12. The working fluid of embodiment 11, wherein the working fluid further comprises a co-solvent.

Embodiment 13. The working fluid of any one of embodiments 11-12, wherein $R_f^1$ and $R_f^2$ form a perfluorinated 6-membered ring, wherein the ring comprises an oxygen atom.

Embodiment 14. The working fluid of any one of embodiments 11-12, wherein ($R_f^1$) and $R_f 2$ form a perfluorinated 5-membered ring.

Embodiment 15. The working fluid of any one of embodiments 11-12, wherein $R_f^1$ is a perfluoro ethyl group and $R_f^2$ is a perfluoro propyl group.

Embodiment 16. The working fluid of any one of embodiments 11-15, wherein $R_H$ is a methyl group.

Embodiment 17. The working fluid of any one of embodiments 11-15, wherein $R_H$ is an ethyl group.

Embodiment 18. The working fluid of any one of embodiments 11-17, wherein the hydrofluorocarboximidate is selected from:

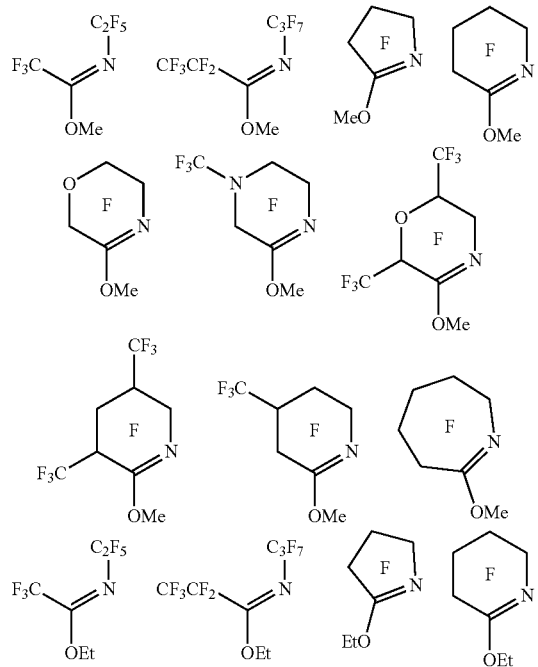

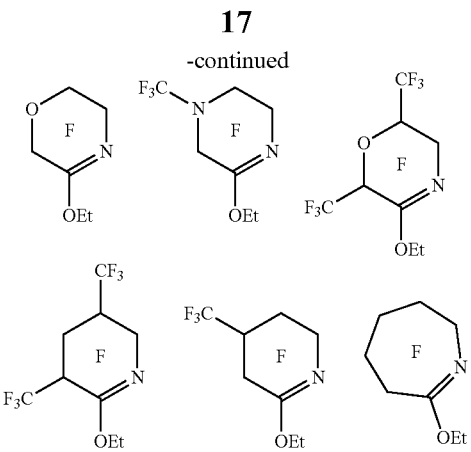

Embodiment 19. Use of a hydrofluorocarboximidate as a cleaning composition, wherein the fluorinated diamine olefin is in a cleaning composition wherein the hydrofluorocarboximidate is of formula (I)

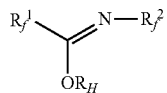

where:
- $R_H$ is a linear or branched alkyl group comprising 1 or 2 carbon atoms; and
- (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 20. Use of a hydrofluorocarboximidate according to embodiment 19, wherein $R_f^1$ and $R_f^2$ form a perfluorinated 6-membered ring, wherein the ring comprises an oxygen atom.

Embodiment 21. Use of a hydrofluorocarboximidate according to embodiment 19, wherein ($R_f^1$) and Rf2 form a perfluorinated 5-membered ring.

Embodiment 22. Use of a hydrofluorocarboximidate according to embodiment 19, wherein $R_f^1$ is a perfluoro ethyl group and $R_f^2$ is a perfluoro propyl group.

Embodiment 23. Use of a hydrofluorocarboximidate according to any one of embodiments 19-22, wherein $R_H$ is a methyl group.

Embodiment 24. Use of a hydrofluorocarboximidate according to any one of embodiments 19-22, wherein $R_H$ is an ethyl group.

Embodiment 25. Use of a hydrofluorocarboximidate according to any one of embodiments 19-24, wherein the hydrofluorocarboximidate is selected from:

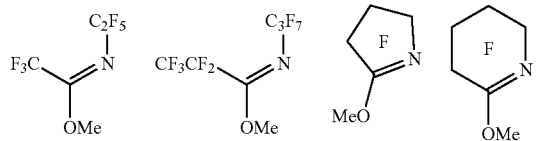

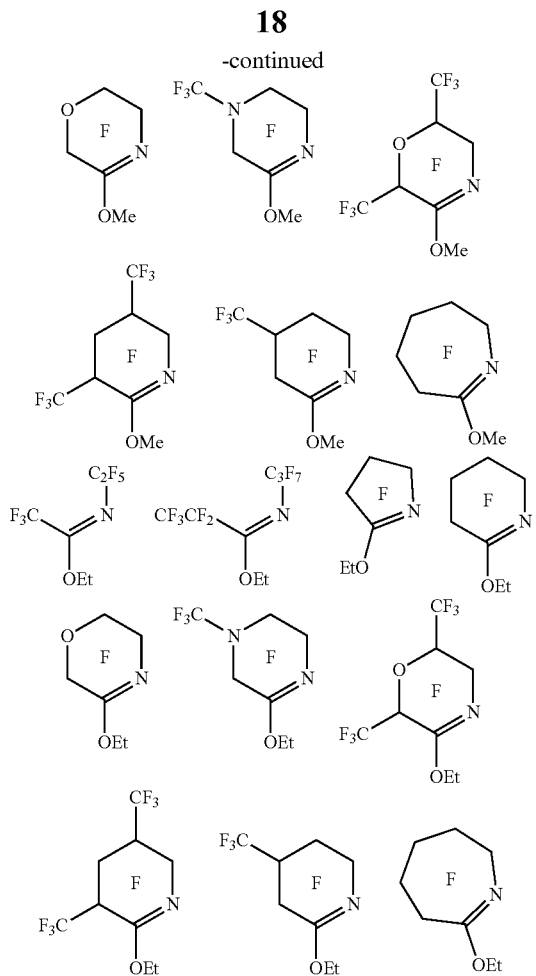

Embodiment 26. Use of a hydrofluorocarboximidate as an electrolyte solvent or additive wherein the hydrofluorocarboximidate is of formula (I)

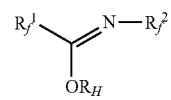

where:
- $R_H$ is a linear or branched alkyl group comprising 1 or 2 carbon atoms; and
- (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 27. Use of a hydrofluorocarboximidate according to embodiment 26, wherein $R_f^1$ and $R_f^2$ form a perfluorinated 6-membered ring, wherein the ring comprises an oxygen atom.

Embodiment 28. Use of a hydrofluorocarboximidate according to embodiment 26, wherein ($R_f^1$) and Rf2 form a perfluorinated 5-membered ring.

Embodiment 29. Use of a hydrofluorocarboximidate according to embodiment 26, wherein $R_f^1$ is a perfluoro ethyl group and $R_f^2$ is a perfluoro propyl group.

Embodiment 30. Use of a hydrofluorocarboximidate according to any one of embodiments 26-29, wherein $R_H$ is a methyl group.

Embodiment 31. Use of a hydrofluorocarboximidate according to any one of embodiments 26-29, wherein $R_H$ is an ethyl group.

Embodiment 32. Use of a hydrofluorocarboximidate according to any one of embodiments 26-31, wherein the hydrofluorocarboximidate is selected from:

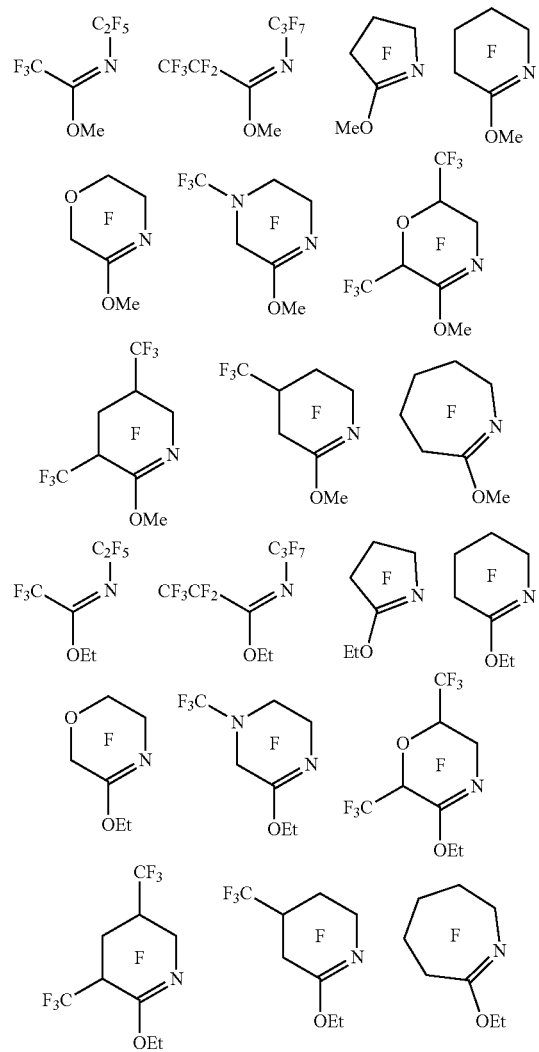

Embodiment 33. Use of a hydrofluorocarboximidate as a heat transfer fluid wherein the hydrofluorocarboximidate is of formula (I)

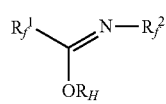

where:
$R_H$ is a linear or branched alkyl group comprising 1 or 2 carbon atoms; and (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof, or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 34. Use of a hydrofluorocarboximidate according to embodiment 33, wherein $R_f^1$ and $R_f^2$ form a perfluorinated 6-membered ring, wherein the ring comprises an oxygen atom.

Embodiment 35. Use of a hydrofluorocarboximidate according to embodiment 33, wherein ($R_f^1$) and Rf2 form a perfluorinated 5-membered ring.

Embodiment 36. Use of a hydrofluorocarboximidate according to embodiment 33, wherein $R_f^1$ is a perfluoro ethyl group and $R_f^2$ is a perfluoro propyl group.

Embodiment 37. Use of a hydrofluorocarboximidate according to any one of embodiments 33-36, wherein $R_H$ is a methyl group.

Embodiment 38. Use of a hydrofluorocarboximidate according to any one of embodiments 33-36, wherein $R_H$ is an ethyl group.

Embodiment 39. Use of a hydrofluorocarboximidate according to any one of embodiments 33-38, wherein the hydrofluorocarboximidate is selected from:

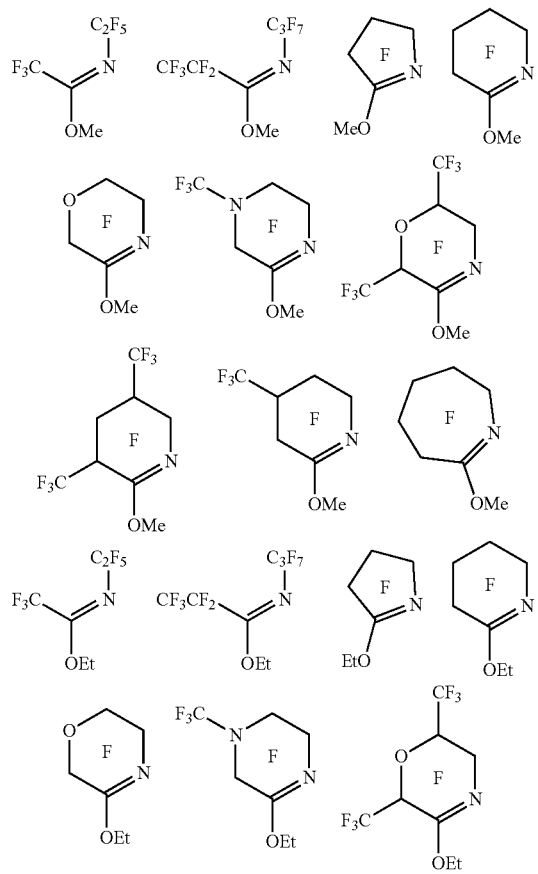

-continued

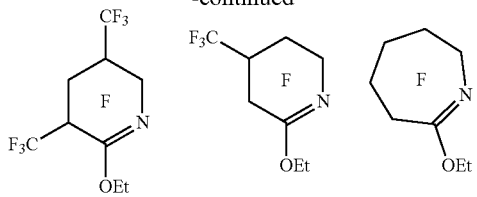

Embodiment 40. An apparatus for heat transfer comprising:
  a device; and
  a mechanism for transferring heat to or from the device, the mechanism comprising a heat transfer fluid that comprises a hydrofluorocarboximidate of formula (I)

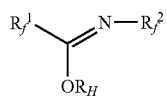

where:
  $R_H$ is a linear or branched alkyl group comprising 1 or 2 carbon atoms; and
  (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 41. An apparatus for heat transfer according to embodiment 40, wherein the device is selected from a microprocessor, a semiconductor wafer used to manufacture a semiconductor device, a power control semiconductor, an electrochemical cell, an electrical distribution switch gear, a power transformer, a circuit board, a multi-chip module, a packaged or unpackaged semiconductor device, a fuel cell, and a laser.

Embodiment 42. An apparatus according to any one of embodiments 40-41, wherein the mechanism for transferring heat is a component in a system for maintaining a temperature or temperature range of an electronic device.

Embodiment 43. A method of transferring heat comprising:
  providing a device; and
  transferring heat to or from the device using a heat transfer fluid that comprises a hydrofluorocarboximidate, wherein the hydrofluorocarboximidate is of formula (I)

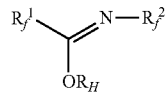

where:
  $R_H$ is a linear or branched alkyl group comprising 1 or 2 carbon atoms; and
  (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

Embodiment 44. A hydrofluorocarboximidate of formula (I)

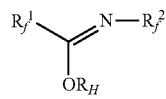

where:
  $R_H$ is a linear or branched alkyl group comprising 1 or 2 carbon atoms; and
  (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof, and wherein the hydrofluorocarboximidate of formula (I) is in a purified form.

EXAMPLES

Unless otherwise noted, all parts, percentages, ratios, etc. in the examples and the rest of the specification are by weight, and all reagents used in the examples were obtained, or are available, from general chemical suppliers such as, for example, Sigma-Aldrich Corp., Saint Louis, Mo., or may be synthesized by conventional methods.

The following abbreviations are used in this section: mL=milliliters, g=grams, mg=milligrams, min=minutes, h=hours, NMR=nuclear magnetic resonance, mol=mole, mmol=millimole, ° C.=degrees Celsius, satd=saturated. Abbreviations for materials used in this section, as well as descriptions of the materials, are provided in Table 1.

TABLE 1

| Material | Details |
|---|---|
| MeOH | Methanol, commercially available from Sigma-Aldrich Corp. |
| EtOH | Ethanol, commercially available from Sigma-Aldrich Corp. |
| NaHCO₃ | Sodium bicarbonate, commercially available from Alfa Aesar. Ward Hill, MA, USA |
| K₂CO₃ | Potassium carbonate, commercially available from Alfa Aesar |

TABLE 1-continued

| Material | Details |
| --- | --- |
| Activated Carbon | Commercially available from Alfa Aesar |
| 4 angstrom molecular sieves | Commercially available from Sigma-Aldrich Corp. |
| Basic alumina | Commercially available from Alfa Aesar |
| 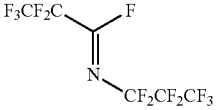<br>2,2,3,3,3,-Pentafluoro-N-(1,1,2,2,3,3,3-heptafluoropropyl)) propanimidoyl fluoride | Can be prepared as described in H.V. Rasika Dias et al. in Dalton Transactions, 2011, vol. 40, page 8569-8580; V. K. Grinevskaja, et al. in Fluorine Notes, 2009, volume 2(63); and A. F. Gontar, et al. in Izvestiya Akademii Nauk SSSR, Seriya Khimicheskaya 1984, vol. 33 issue 8, pages 1711-1714. |
| 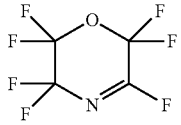<br>2,2,3,3,5,6,6-heptafluoro-3,6-dihydro-2H-1,4-oxazine | |
| 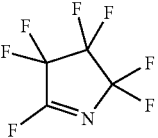<br>2,2,3,3,4,4,5-heptafluoro-3,4-dihydro-2H-pyrrole | |
| B(OMe)$_3$ | Trimethylborate, commercially available from Sigma-Aldrich Corp. |
| B(OEt)$_3$ | Triethylborate, commercially available from Sigma-Aldrich Corp. |
| 1,1-dimethylpropyl 2-ethylhexaneperoxoate | Available under the trade designation "LUPEROX 575" from Arkema, Crosby, TX |
| TAPEH | tert-Amylperoxy-2-ethylhexanoate, available as LUPEROX 575 from Arkema, Crosby, TX, USA |
| Silica gel | Commercially available from Sigma-Aldrich Corp. |
| Acetone | Commercially available from Sigma-Aldrich Corp. |
| Water | De-ionized water |

Example 1 (EX-1) Preparation of 5-ethoxy-2,2,3,3,6,6-hexafluoro-3,6-dihydro-2H-1,4-oxazine F

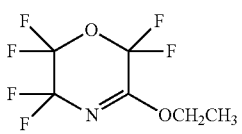 [SMILES: CCOC1=NC(F)(F)C(F)(F)OC1(F)F]

A 300 mL Parr reactor was charged with EtOH (42.0 g, 0.91 mol). The reactor was then sealed and cooled by submersion in a dry ice-acetone bath followed by the addition of 2,2,3,3,5,6,6-heptafluoro-3,6-dihydro-2H-1,4-oxazine (27.8 g, 132 mmol). Stirring commenced and the reaction mixture was slowly heated. When heated, the internal pressure slowly rose to 50 psig (345 kPa above atmosphere) and once the temperature reached 65° C., the pressure had dropped to ambient. The reaction mixture was heated to 75° C. and allowed to stir overnight. The reaction mixture was then cooled to room temperature and then quenched by the addition of saturated NaHCO$_3$ solution in water (100 mL) and then further diluted by water (50 mL). The bottom fluorous phase was separated, giving a crude mixture containing approximately 33% of 5-ethoxy-2,2,3,3,6,6-hexafluoro-3,6-dihydro-2H-1,4-oxazine as indicated by GC-FID (gas chromatography-flame ionization detection) analysis. Formation of 5-ethoxy-2,2,3,3,6,6-hexafluoro-3,6-dihydro-2H-1,4-oxazine was confirmed by GC-MS (gas chromatography-mass spectrometry) analysis.

Example 2 (EX-2) Preparation of 5-ethoxy-2,2,3,3,6,6-hexafluoro-3,6-dihydro-2H-1,4-oxazine A 300 mL Parr reactor was charged with B(OEt)$_3$ (41.9 g, 287 mmol) and 1,1-dimethylpropyl 2-ethylhexaneperoxoate (2.3 g, 10 mmol). The reaction vessel was then sealed and placed in an acetone/dry ice bath followed by addition of 2,2,3,3,5,6,6-heptafluoro-3,6-dihydro-2H-1,4-oxazine (31.3 g, 148 mmol). The vessel was then slowly heated to 75° C. with stirring. The pressure began to rise at 50° C. Once the reaction temperature reached 65° C., the vessel had dropped to ambient pressure. The reaction mixture was allowed to stir at 75° C. overnight. The temperature was then raised to 90° C. and allowed to stir for 20 min at that temperature. The reaction mixture was then allowed to cool to room temperature and was transferred to a 500 mL Erlenmeyer flask with a stir bar. Saturated NaHCO$_3$ solution in water was slowly added followed by addition of 50 mL water. The bottom fluorous phase was split and GC-FID analysis of the crude material indicated the title compound in 87% purity with <1% formation of other hydrofluorocarboximidate materials. GC-MS and NMR analyses confirmed the mass and structure of 5-ethoxy-2,2,3,3,6,6-hexafluoro-3,6-dihydro-2H-1,4-oxazine. Purification via single-plate distillation afforded 5-ethoxy-2,2,3,3,6,6-hexafluoro-1,4-oxazine (32.5 g, 92.4% Yield) as a colorless liquid.

Example 3 (EX-3) Preparation of ethyl 2,2,3,3,3-pentafluoro-N-(perfluoropropyl)propanimidate

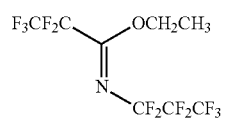

To a 3-neck round-bottom flask equipped with a temperature probe and magnetic stir bar was added $K_2CO_3$ (1.28 g, 9.26 mmol) and 2,2,3,3,3-Pentafluoro-N-(perfluoropropyl)propanimidoyl fluoride (4.95 g, 14.9 mmol). To the mixture was added EtOH (0.92 mL, 16 mmol) dropwise over the course of 1 h. Exotherms as high as 35° C. were observed. After an overnight stir was allowed, the reaction contents were analyzed by GC. Complete conversion of the starting material was observed with ethyl 2,2,3,3,3-pentafluoro-N-(perfluoropropyl)propanimidate accounting for approximately 60% of the crude reaction product mixture.

Example 4 (EX-4) Preparation of ethyl 2,2,3,3,3-pentafluoro-N-(perfluoropropyl)propanimidate To a mixture of $B(OEt)_3$ (4.38 g, 30.0 mmol) and 2,2,3,3,3-Pentafluoro-N-(perfluoropropyl)propanimidoyl fluoride (10 g, 30.0 mmol) with magnetic stirring was slowly added saturated $NaHCO_3$ in water (20 mL). Exotherms were observed as a result of hydrolysis of the $B(OEt)_3$. After a 1 h stir at room temperature following complete addition of $NaHCO_3$ in water (20 mL), the fluorous phase was separated and analyzed by GC-FID. A substantial amount of EtOH was observed. After a subsequent water wash, most EtOH was removed and again analyzed by GC-FID. Ethyl 2,2,3,3,3-pentafluoro-N-(perfluoropropyl)propanimidate was present in 87% purity (79% yield by GC-FID analysis) with <1% formation of other hydrofluorocarboximidate materials. The preparation of ethyl 2,2,3,3,3-pentafluoro-N-(perfluoropropyl)propanimidate product was confirmed by GC-MS analysis.

Example 5 (EX-5) Preparation of methyl 2,2,3,3,3-pentafluoro-N-(perfluoropropyl)propanimidate

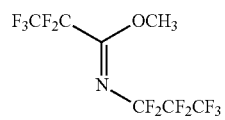

To a 500 mL round bottom flask equipped with a stir bar and addition funnel, were added 2,2,3,3,3-pentafluoro-N-(perfluoropropyl)propanimidoyl fluoride (205 g, 616 mmol) and $K_2CO_3$ (51 g, 369 mmol). To the resultant stirring mixture, was slowly added MeOH (38 mL, 939 mmol) over the course of 30 min. The resultant mixture was allowed to stir for 3 h before the addition of water (100 mL). The mixture was filtered and then phase split. The fluorous layer was collected to give a crude mass of 83 g. GC-FID analysis indicated that 30% of the crude mixture was methyl 2,2,3,3,3-pentafluoro-N-(perfluoropropyl)propanimidate (24.9 g, 12% yield).

Example 6 (EX-6) Preparation of methyl 2,2,3,3,3-pentafluoro-N-(perfluoropropyl)propanimidate To a 500 mL round-bottom flask equipped with a stir bar, Claisen head, and water-cooled condenser, and addition funnel, was added $B(OMe)_3$ (23.4 g, 225 mmol), 2,2,3,3,3-pentafluoro-N-(1,1,2,2,3,3,3-heptafluoropropyl)propanimidoyl fluoride (150 g, 450 mmol), and $K_2CO_3$ (37.4 g, 270 mmol). The mixture was stirred at room temperature followed by the dropwise addition of water (50 mL) over the course of 1 h to avoid excess exotherms. After complete addition, the resultant reaction mixture was allowed to stir for one additional h. The mixture was then diluted with water (200 mL) and filtered. The filtrate was transferred to a separatory funnel and the fluorous phase was collected and then washed with water (2×100 mL). The fluorous phase was then passed over a pad of silica gel and GC-FID analysis of the filtrate indicated that the crude material consisted of >83% of methyl 2,2,3,3,3-pentafluoro-N-(1,1,2,2,3,3,3-heptafluoropropyl)propanimidate with <1% formation of other hydrofluorocarboximidate materials. The filtrate was then purified by fractional distillation (119° C.) to afford methyl 2,2,3,3,3-pentafluoro-N-(1,1,2,2,3,3,3-heptafluoropropyl)propanimidate (129 g, 83% yield). The preparation of methyl 2,2,3,3,3-pentafluoro-N-(1,1,2,2,3,3,3-heptafluoropropyl)propanimidate was confirmed by GC-MS analysis.

Example 7 (EX-7) Preparation of 5-ethoxy-2,2,3,3,4,4-hexafluoro-3,4-dihydro-2H-pyrrole

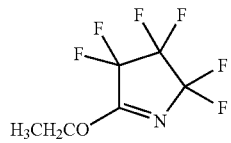

To a 3-neck 250 mL round-bottom flask equipped with a stir bar, dry ice/acetone condenser, and addition funnel, was added $B(OMe)_3$ (8.0 g, 77 mmol) and $K_2CO_3$ (12.8 g, 92). The mixture was cooled to 0° C. with an ice bath. To the mixture was added 2,2,3,3,4,4,5-heptafluoro-3,4-dihydro-2H-pyrrole (30 g, 154 mmol) and water (20 g) in portions over 1 h. The resultant mixture was allowed to rise to room temperature followed by an overnight stir. The mixture was then filtered followed by separation of the fluorous phase to give 25.7 g of a crude mixture. GC-FID analysis indicated that the crude mixture contained approximately 89% of 5-ethoxy-2,2,3,3,4,4-hexafluoro-3,4-dihydro-2H-pyrrole (72% yield by GC-FID analysis) with <1% formation of other hydrofluorocarboximidate materials. Preparation of 5-ethoxy-2,2,3,3,4,4-hexafluoro-3,4-dihydro-2H-pyrrole was confirmed by GC-MS analysis.

Example 8 (EX-8) Thermal stability of methyl 2,2,3,3,3-pentafluoro-N-(perfluoropropyl)propanimidate Thermal stability was measured by charging 1 g of EX-6 into each of six glass vials and then adding 100 mg of absorbent as indicated in Table 2, below. The samples were stirred for 24 h at 50° C. and then analyzed for purity by GC-FID. The % purity EX-6 initially was 97.7%. Shown in Table 2 below are the % purity after the thermal stability test. All of the results are within error of the test method.

TABLE 2

Thermal Stability Results

| No Absorbent | No Absorbent | Activated Carbon | 4 Angstrom Molecular Sieves | $K_2CO_3$ | Basic Alumina | Silica Gel |
|---|---|---|---|---|---|---|
| Purity (%) | 97.7 | 98.2 | 98.0 | 97.9 | 98.0 | 97.9 |

Foreseeable modifications and alterations of this invention will be apparent to those skilled in the art without departing from the scope and spirit of this invention. This invention should not be restricted to the embodiments that are set forth in this application for illustrative purposes. To the extent that there is any conflict or discrepancy between this specification as written and the disclosure in any document mentioned or incorporated by reference herein, this specification as written will prevail.

What is claimed is:

1. A method of making of a hydrofluorocarboximidate comprising:
   contacting a perfluorinated imine with a trialkyl borate in the presence of base to form a hydrofluorocarboximidate of formula (I)

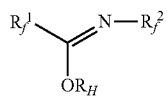

where:
   $R_H$ is a linear or branched alkyl group comprising 1 or 2 carbon atoms; and
   (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

2. The method of claim 1, wherein $R_f^1$ and $R_f^2$ form a perfluorinated 6-membered ring, wherein the ring comprises an oxygen atom.

3. The method of claim 1, wherein ($R_f^1$) and $R_f^2$ form a perfluorinated 5-membered ring.

4. The method of claim 1, wherein $R_f^1$ is a perfluoro ethyl group and $R_f^2$ is a perfluoro propyl group.

5. The method of claim 1, wherein $R_H$ is a methyl group.

6. The method of claim 1, wherein $R_H$ is an ethyl group.

7. The method of claim 1, wherein the hydrofluorocarboximidate is selected from:

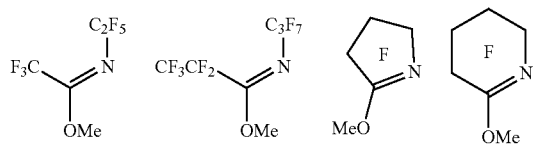

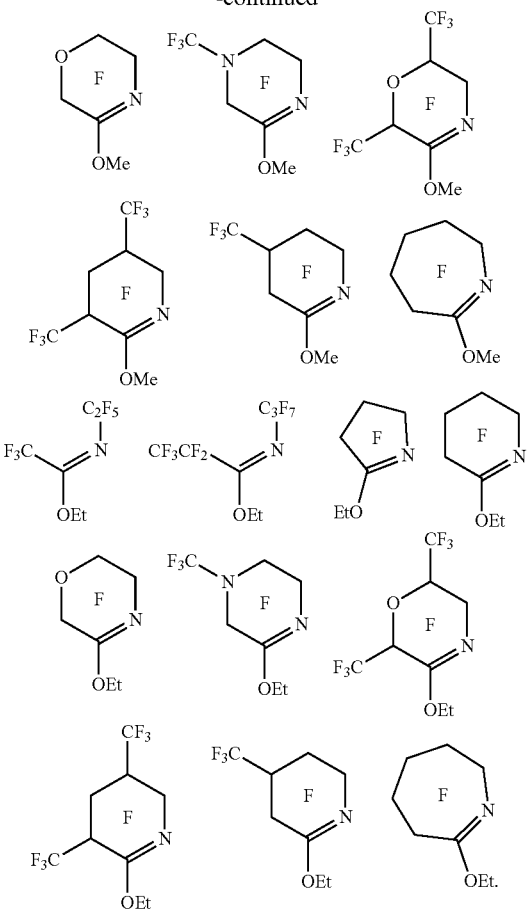

8. A working fluid comprising a hydrofluorocarboximidate wherein the hydrofluorocarboximidate is present in the working fluid in an amount of at least 25% by weight based on the total weight of the working fluid and the hydrofluorocarboximidate is of formula (I)

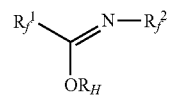

where:
   $R_H$ is a linear or branched alkyl group comprising 1 or 2 carbon atoms; and
   (a) $R_f^1$ and $R_f^2$ are independently selected from a linear or branched perfluorinated alkyl group comprising 1-8 carbon atoms and optionally comprising at least one catenated atom selected from oxygen, nitrogen, or combinations thereof; or (b) $R_f^1$ and $R_f^2$ are connected to form a ring structure comprising a total of 4-8 carbon atoms and optionally comprising at least one catenated atom selected from oxygen, nitrogen, or a combination thereof.

9. The method of claim 1, wherein the hydrofluorocarboximidate based on closed-cup flashpoint testing following ASTM D-327-96 e-1 is not flammable.

10. The method of claim 1, wherein the hydrofluorocarboximidate has a global warming potential of less than 100.

11. The method of claim 1, wherein the hydrofluorocarboximidate has a boiling point of 80 to 150C.

12. The working fluid of claim 8, wherein the working fluid further comprises a co-solvent.

13. The working fluid of claim 8, wherein $R_f^1$ and $R_f^2$ form a perfluorinated 6-membered ring, wherein the ring comprises an oxygen atom.

14. The working fluid of claim 8, wherein $R_f^1$ and Rf2 form a perfluorinated 5-membered ring.

15. The working fluid of claim 8, wherein $R_f^1$ is a perfluoro ethyl group and $R_f^2$ is a perfluoro propyl group.

16. The working fluid of claim 8, wherein $R_H$ is a methyl group.

17. The working fluid of claim 8, wherein $R_H$ is an ethyl group.

18. The working fluid of claim 8, wherein the hydrofluorocarboximidate is selected from:

* * * * *